United States Patent [19]

Miller et al.

[11] Patent Number: 4,821,722
[45] Date of Patent: Apr. 18, 1989

[54] SELF-VENTING BALLOON DILATATION CATHETER AND METHOD

[75] Inventors: Gary H. Miller, Milpitas; Wilfred J. Samson, Saratoga, both of Calif.

[73] Assignee: Advanced Cardiovascular Systems, Inc., Mountain View, Calif.

[21] Appl. No.: 651

[22] Filed: Jan. 6, 1987

[51] Int. Cl.⁴ .................................. A61M 29/02
[52] U.S. Cl. ............................ 128/344; 604/96; 128/348.1
[58] Field of Search ............. 128/334, 348.1; 604/96, 604/99, 118, 122, 348.1

[56] References Cited

U.S. PATENT DOCUMENTS

| | | | |
|---|---|---|---|
| 3,482,576 | 12/1969 | Ericson et al. | 604/99 |
| 3,640,282 | 2/1972 | Kamen et al. | 128/344 |
| 3,742,960 | 7/1973 | Dye et al. | 604/99 |
| 3,794,036 | 2/1974 | Carroll | 128/207.15 |
| 4,349,033 | 9/1982 | Eden | 604/96 |
| 4,576,590 | 3/1986 | Fiddian-Green | 604/96 |
| 4,582,181 | 4/1986 | Samson | 128/348.1 |
| 4,597,755 | 7/1986 | Samson et al. | 604/96 |
| 4,638,805 | 1/1987 | Powell | 128/344 |
| 4,715,378 | 12/1987 | Poper, Jr. et al. | 128/344 |

Primary Examiner—Dalton L. Truluck
Assistant Examiner—Kathleen A. Daley
Attorney, Agent, or Firm—Fulwider, Patton, Rieber, Lee & Utecht

[57] ABSTRACT

Self-venting balloon dilatation catheter having an elongate flexible tubular member having at least one lumen therein extending longitudinally thereof. A balloon is carried by the flexible tubular member and is in communication with the lumen. A fitting is carried by the tubular member for inflating the balloon with a balloon inflating medium. A plurality of small passages are formed which permit air to escape from the interior of the balloon but inhibit the passage of the balloon inflation medium from the balloon.

12 Claims, 3 Drawing Sheets

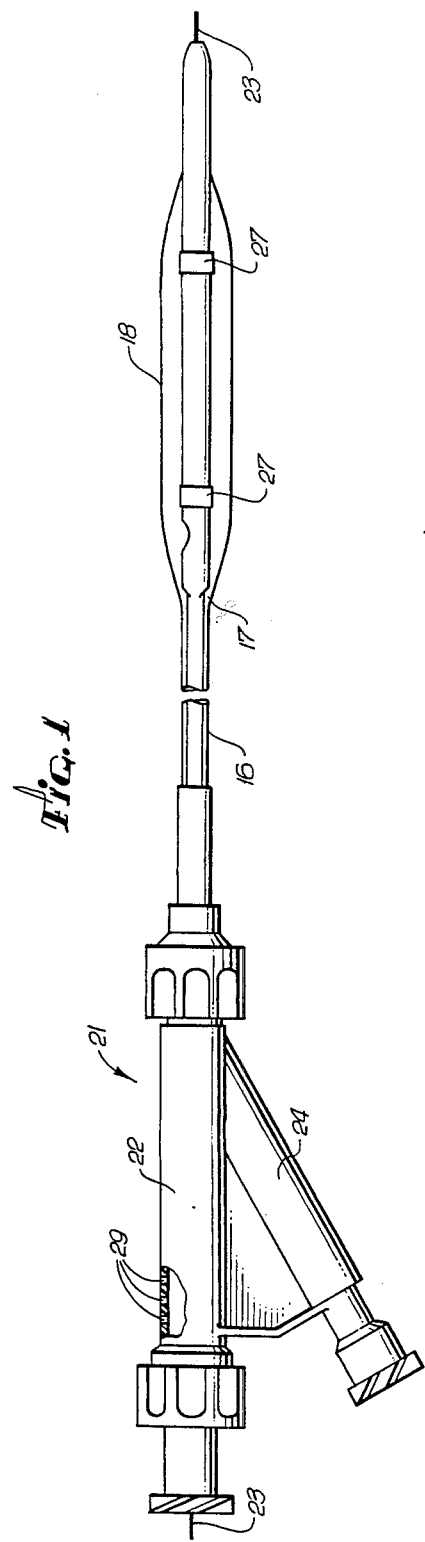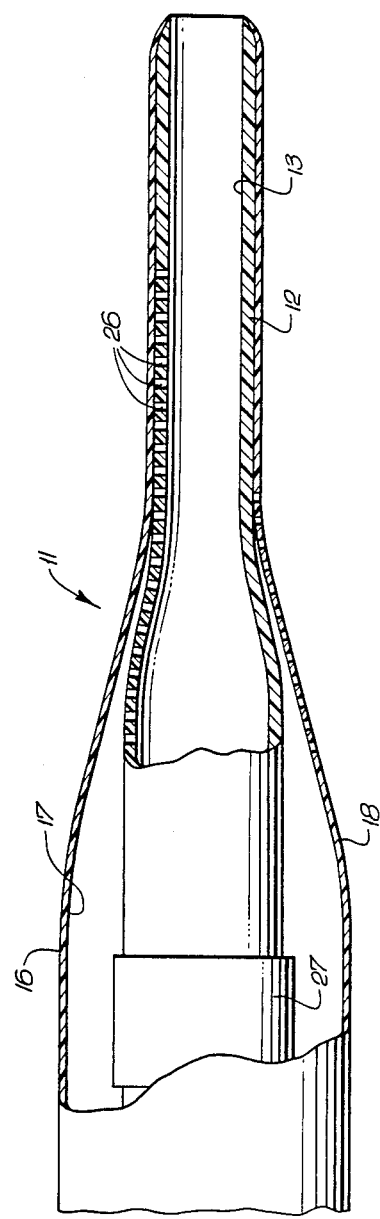

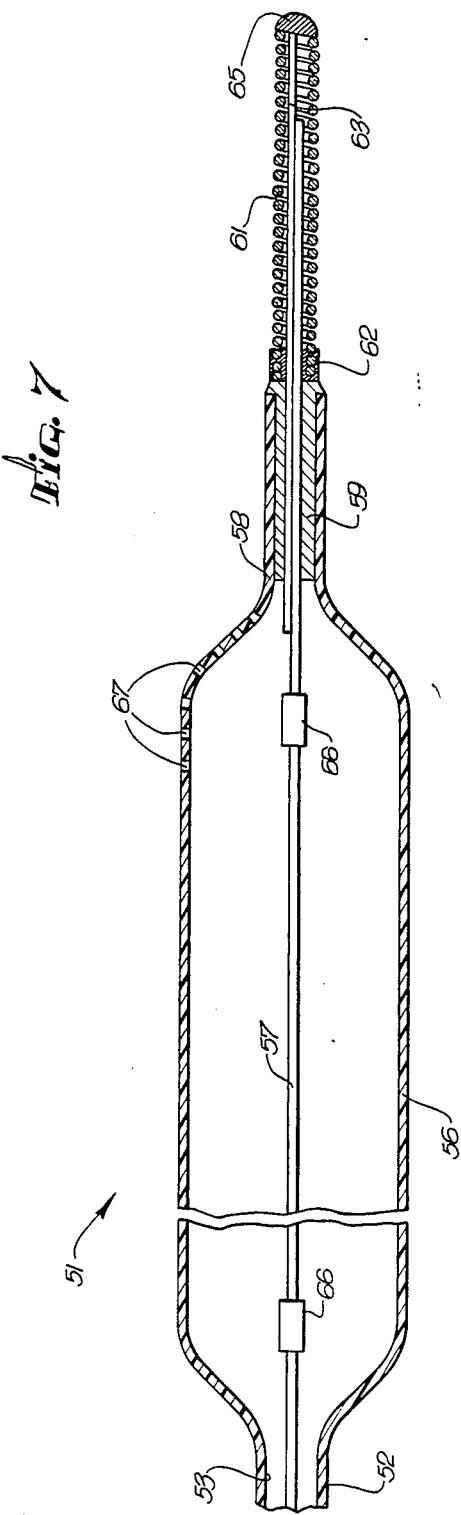

SELF-VENTING BALLOON DILATATION CATHETER AND METHOD

This invention relates to a self-venting balloon dilatation catheter and method.

Self-venting balloon dilatation catheters have heretofore been provided of the type disclosed in U.S. Pat. application Ser. No. 760,637, filed July 30, 1985. In manufacturing such self-venting balloon dilatation catheters difficulties have been encountered in manufacturing such catheters, particularly, in certain sizes. For example, problems have been encountered in inserting and removing the mandrel utilized for forming the hole for the self-vent. In addition, it has been found that air may be trapped in the adapter during balloon inflations. There is therefore a need for a new and improved self-venting balloon dilatation catheter and method for making the same.

In general, it is an object of the present invention to provide a self-venting balloon dilatation catheter and method in which self-venting is achieved by providing a plurality of holes which permit air to pass therethrough but which will not permit the passage of the ballon inflation medium.

Another object of the invention is to provide a balloon dilatation catheter of the above character in which micro-machined holes are utilized.

Another object of the invention is to provide a balloon dilatation catheter of the above character in which micro-machined holes can be placed in a myriad of locations and patterns.

Another object of the invention is to provide a balloon dilatation catheter of the above character in which the self-venting holes are provided in the inner tubular element.

Another object of the invention is to provide a balloon dilatation catheter of the above character in which the holes are provided in the balloon.

Another object of the invention is to provide a balloon dilatation catheter of the above character in which self-venting holes are placed in the adapter at the proximal extremity of the catheter.

Another object of the invention is to provide a balloon dilatation catheter of the above character in which a single lumen as well as a double lumen can be utilized.

Another object of the invention is to provide a balloon dilatation catheter of the above character in which the holes are provided by the use of porous materials forming the area of the catheter in which self-venting is to take place.

Another object of the invention is to provide a balloon dilatation catheter of the above character which can be readily manufactured with repeatable characteristics.

Additional objects and features of the invention will appear from the following description in which the preferred embodiments are set forth in conjunction with the accompanying drawings.

FIG. 1 is a side elevational view of a self-venting balloon dilatation catheter incorporating the present invention using a movable guide wire with self-venting holes for the balloon and in the adapter.

FIG. 2 is an enlarged portion of the distal extremity of the balloon dilatation catheter shown in FIG. 1 with certain portions being shown in cross section and particularly, showing the use of inner and outer tubular members and vent holes in the inner tubular member.

FIG. 7 is a cross-sectional view of another embodiment of a self-venting balloon dilatation catheter using a single lumen and a fixed guide wire.

Figure 3:
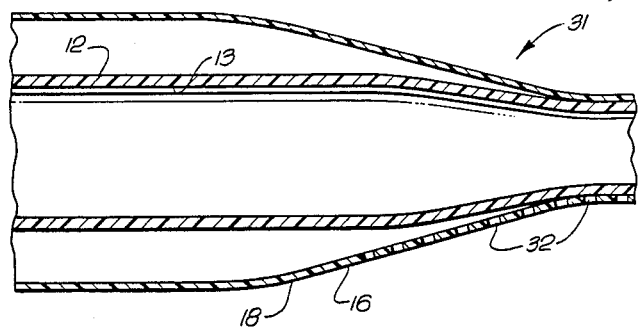
FIG. 3 is a cross-sectional view similar to FIG. 2 but showing the vent holes in the balloon.

In general, the self-venting balloon dilatation catheter of the present invention is comprised of an elongate flexible tubular member having a flow passage therein. An inflatable balloon is carried by the tubular member. The tubular member and the balloon serve as first and second parts of the balloon dilatation catheter. Means is carried by one or both of the first and second parts which provides a plurality of small passages permitting air to escape from the balloon while retaining the balloon inflation medium within the balloon. Self-venting holes or passages are also provided in the adapter. Various structures and methods are utilized to provide the plurality of small passages.

More particularly, as shown in the drawing, the self-venting balloon dilatation catheter 11 consists of an inner or first tubular member 12 which is provided with a flow passage or lumen 13 extending longitudinally thereof. As also shown in FIG. 2, the passage 13 extends through the distal extremity of the tubular member 12. The tubular member 12 can be formed of a suitable plastic such as that described in U.S. Pat. No. 4,323,071.

The catheter 11 also consists of an outer or second tubular member 16 which is disposed coaxially on the inner tubular member 12. The tubular member 16 also can be formed of a suitable plastic material such as that disclosed in U.S. Pat. No. 4,323,071. An annular flow passage or lumen 17 is provided between the inner tubular member 12 and the outer tubular member 17 and extends longitudinally of the same. The annular flow passage 17 opens into an integral balloon 18 provided in the distal extremity of the catheter 11. The balloon is formed in the manner described in U.S. Pat. No. 4,323,071. The distal extremity of the second outer tubular member 16 is bonded to the outer surface of the inner tubular member 12 to provide a fluid-tight seal between the same in the manner described in U.S. Pat. No. 4,323,071. As can be seen from FIGS. 1 and 2 of the drawing, the distal extremity of the catheter 11 is slightly rounded at the distal extremity to facilitate insertion of the catheter into a vessel in the human body. The inner tubular member 12 and the outer tubular member 16 with its integral balloon provide first and second parts respectively.

The proximal extremities of the inner and outer tubular members 12 and 16 are connected to a conventional two-arm adapter 21 in which a center arm 22 is provided through which a guide wire 23 extends. The center arm 22 is in communication with the flow passage 13 in the inner tubular member 12 so that the guide wire can extend through the catheter and be utilized for positioning the catheter as disclosed in U.S. Pat. No. 4,323,071. The annular flow passage 17 is in communication with the side arm 24 and is adapted to receive the inflation medium which can be introduced through the side arm 24 in a conventional manner to pass through the annular flow passage 17 for inflating and deflating the balloon 18.

Self-venting means is carried by one or both of said first and second parts forming a plurality of small passages for permitting air to escape through said one or both parts from the balloon to ambient while retaining the balloon inflating medium in the balloon. Such means consists of a plurality of micro-machined holes 26 which serve to establish communication with the interior of the balloon 18 and the inner passage 13 of the inner tubular member 12. The micro-machined holes 26 can be provided in a predetermined pattern. For example as shown in FIG. 2, the holes 26 can be provided in a suitable pattern such as in a line extending form a region near the distal extremity of the catheter to a region which is within the interior of the balloon 18. It should be appreciated that the holes can be placed anywhere along the working length of the balloon including the proximal. The micromachined holes 26 can be of a suitable size as, for example, ranging from 0.0005 inches to 0.0010 inches in diameter with the holes being spaced apart a suitable distance as, for example, for 0.001 to 0.100 inches, Although the holes 36 have boon shown as being in line, the holes 20 can be arranged in other desired patterns as, for example, in a helical path, staggered or otherwise. The holes can extend through plastic of various wall thicknesses as, for example, ranging from 0.0002 to 0.100 inches. It has been found that holes of this size can be readily formed in various types of plastics as, for example, polyethylene, polyesters, polyurethanes and polypropylenes. The micro-machined holes 26 can be formed in a suitable manner such as by the use of a laser.

It is desirable to provide such holes 26 so that they extend longitudinally of the catheter. It is also desirable that they extend longitudinally of the distal extremity of the balloon so that the air in the balloon can be readily vented to the atmosphere. It can be seen that as the inflation medium is introduced into the balloon, any air in the balloon inflation lumen and the balloon is pushed forwardly into and in the balloon and will progressively vent through the micro-machined holes 26 so that the balloon can be inflated rapidly with an inflation medium and also so that any air therein can readily escape. With the holes arranged longitudinally in this manner, it is not essential that every micro-machined hole 26 be open because there is more than adequate ventilation provided by the plurality of holes 26. This facilitates bonding of the distal extremity of the outer tubular member 16 to the inner tubular member 12. Even if one or more of the micro-machined holes are covered, this will not unduly interfere with the venting of air to the atmosphere. The micro-machined holes 26 are of such a size so that the inflation medium, as for example, a typically radiopaque liquid or a saline water mixture cannot pass through the holes 26 because of the size of the holes. The inflation medium which is utilized in the balloon cannot pass through the very small micro-machined holes 26 because of the surface tension which occurs when the holes are wetted by the inflation medium. In other words, a miniscus is established across each hole to establish a zero velocity region and prevents the liquid inflation medium from escaping through the hole. Thus, even though the air in the balloon can escape through the holes, the inflating medium utilized for the balloon cannot escape through the holes.

It has been found that the use of such micro-machined holes readily facilitates evacuation of air from the balloon during filling of the balloon, while at the same time preventing the inflation medium from passing from the balloon so that a suitable pressure can be maintained on the balloon.

A pair of radiopaque markers 27 formed of a suitable material such as gold or tungsten are positioned on the exterior of the inner tubular member 12 and are spaced apart so that they are near the proximal and distal extremities of the balloon to indicate the working length (the straight portion of the balloon). These radiopaque markers as shown are in the form of rings.

Self-venting means can also be provided in the adapter for permitting the escape of air entrapped in the adapter 21 and in particular the central arm 22 upon the first inflations of the balloon 18. This self-venting means as with the balloon can take the form of a plurality of small spaced apart holes or passages 29 (see FIG. 1) provided in the center arm 22 adjacent the proximal extremity thereof. These small holes or passages can be arranged in any desired predetermined pattern. As can be seen when the balloon 18 is filled any air trapped in the proximal extremity of the center arm 22 will be vented to the atmosphere in the same way air is vented from the balloon 18. Thus, the entire catheter will be free of entrapped air.

Another embodiment of a catheter 31 incorporating the present invention shown in FIG. 3 has a construction very similar to that provided in FIGS. 1 and 2 with the exception that the micro-machined holes 32 are provided in the balloon 18 itself, rather than in the inner tubular member 12. As also can be seen from FIG. 3, these micro-machined holes 32 are arranged in a row which extends from the distal extremity of the balloon toward an intermediate portion of the balloon. It should be appreciated that these holes 32 can be arranged in a myriad of patterns and still be functional. As the balloon 18 is inflated with an inflation medium, the inflation medium will push the air in the balloon forwardly so that it can escape through the micro-machined holes. The last amount of air can escape through the last hole 32 provided in the balloon. The balloon can have a suitable wall thickness such as 0.0002 to 0.100 inches with the micro-machined holes having a diameter ranging from 0.00005 to 0.001 inches. The inner tubular member 12 can have a wall thickness ranging from 0.001 to 0.100 inches.

Figure 4:
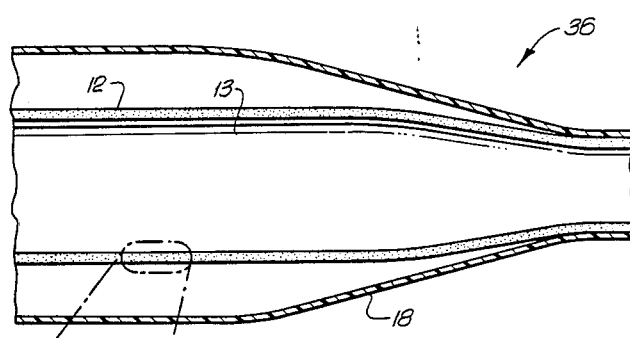
FIG. 4 is another cross-sectional view similar to FIG. 2 but showing the inner member being formed of a fabricated porous material to provide the vent holes.
Figure 4A:
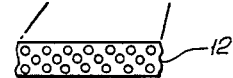
FIG. 4A is an enlarged cross-sectional view of a portion of the member 12 shown in FIG. 4.

Still another embodiment of a catheter 36 incorporating the present invention is shown in FIG. 4 and consists of a construction also very similar to that described in FIGS. 1 and 2. In this embodiment of the invention, the member 12 is formed of a porous plastic material which is provided with a micro structure of holes providing circuitous small passages extending through the same. Suitable materials can be in the form of porous polypropylene and polyethlene materials. Such materials also have the characteristic of permitting air to pass through the same but after becoming wetted will prevent the passage of liquids as, for example, a liquid balloon inflation medium passing through the same.

Figure 5:
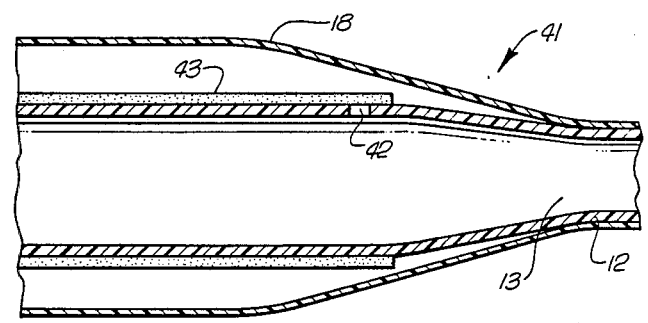
FIG. 5 is another cross-sectional view similar to FIG. 2 showing a porous material covering an opening in the inner tubular member to provide the vent holes.

Still another embodiment of a catheter 41 incorporating the present invention is shown in FIG. 5 in which the inner member 12 is provided with a port or large hole 42 which establishes communication with the passage 13 in the inner tubular member 12 and the interior of the balloon 18. This port or large hole 42 can be covered by a layer 43 of a porous plastic material of the type hereinbefore described which is provided with a plurality of small circuitous passages. The layer 43 can be formed in a suitable manner such as by heat shrinking the same over the opening or port 42 or alternatively, it can be adhesively secured to the outer wall of the inner member 12 so that it immediately overlies the port 42.

It can be seen that the operation of the embodiment of the invention is very similar to that hereinbefore described in that as the balloon inflation medium is introduced into the balloon 18, air within the balloon will be forced toward the distal, or if the catheter was inverted, proximal extremity of the balloon where it will exit through the porous material and through the port 42 and through the passage 13 until substantially all the air has been removed from the balloon during inflation of the same. The hole 42 can have a suitable size, for example, ranging from 0.001 to 0.100 inches. It should be appreciated that if desired the position of the balloon 18 can be inverted during filling in which case the port 42 can be placed in the proximal extremity of the balloon 18.

Figure 6:
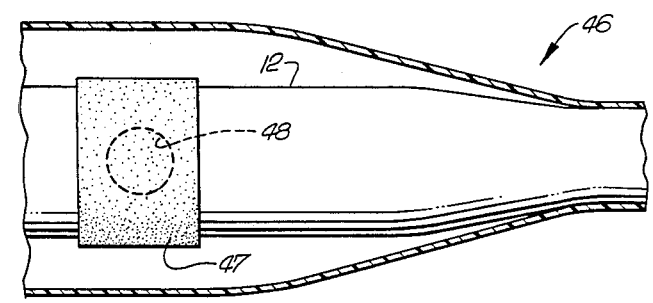
FIG. 6 is another cross-sectional view similar to FIG. 2 showing a porous material covering the opening in the inner member and also serving as a radiopaque marker.

Still another embodiment of a catheter 46 incorporating the present invention is shown in FIG. 6 in which a metal band 47 is provided formed of a porous material which overlies a hole or port 48 provided in the inner member 12. The band 47 being formed of a porous metal again would provide a circuitous path in the form of small passages for the exit of air from the interior of the balloon into the passage 13 of the inner member 12. At the same time, the porous metal member or band 47 can serve an additional purpose. Since it is formed of a radiopaque material such as tungsten or platinum and the like, it also can serve as a radiopaque marker for facilitating the position of the balloon of the dilatation catheter. Such a metal band also can be formed of gold. It can be seen as the balloon is inflated with an inflation medium, air trapped within the balloon will move towards the distal extremity and will be exhausted through the porous metal member 47 and through the opening 48 and through the passage 13 to the atmosphere. The hole 48 also can have a suitable size, for example, ranging from 0.001 to 0.100 inches.

In the foregoing embodiments of the self-venting dilatation catheter described in FIGS. 1-6, a dilatation catheter of the type utilizing coaxial lumen construction with an integral balloon has been disclosed. The present invention is also applicable to dilatation catheters of the type which do not utilize a coaxial lumen construction as, for example, in which the lumens are provided in which the flexible elongate element is provided with two passages in the same at the same time that it is extruded which lumens or passages may lie side by side in cross section with the balloon inflation lumen having a smaller size than the lumen through which the guide wire is passed. With such a construction a separate balloon, rather than an integral balloon, can be utilized. The separate balloon can be adhered to the distal extremity of the flexible elongate tubular member in a manner well known to those skilled in the art and as utilized by balloon dilatation catheters presently in the market. It should be appreciated that certain types of catheters can have an inflation lumen larger than the guide wire lumen.

In addition, it should be appreciated that the present self-venting concept, for balloon dilatation catheters can also be utilized with balloon dilatation catheters having fixed guide wires in which only a single lumen is required. This is particularly desirable for low-profile balloon dilatation catheters. Such a balloon dilatation catheter is described in detail in U.S. Pat. No. 4,582,181. In addition such a construction is shown in FIG. 7.

As shown in FIG. 7, the self-venting balloon dilatation catheter 51 incorporating the present invention consists of an elongate flexible tubular member 52 having an inner lumen 53 extending from the proximal extremity thereof to the distal extremity. An inflatable balloon 56 is formed on the distal extremity of the tubular member 52 and is formed integral therewith. However, as previously explained it should be appreciated that if desired a separate balloon can be provided which can have its proximal extremity adhered to the tubular member 52 by suitable means such as an adhesive.

A fixed guide wire 57 extends through the lumen 53 and through the balloon 56 and through the distal extremity 58 of the tubular member 52. The distal extremity of he balloon and the distal portion 58 of the tubular member 52 can be secured to the guide wire by suitable means such as an adhesive 59. The distal extremity of the guide wire is tapered to provide additional flexibility. A coil spring 61 is mounted on the distal extremity of the guide wire 57 and can be secured thereto by suitable means such as solder 62. The coil spring 61 is of a length so that it extends beyond the distal extremity of the guide wire 57. A shaping ribbon 63 formed of a suitable material such as tungsten extends along the guide wire 57 into the distal extremity of the balloon 56 and is secured therein by the adhesive 59 and the solder joint 62. The shaping ribbon 63 extends beyond the distal extremity of the guide wire 57 and has its distal extremity secured to the distal extremity of the coil spring 61 by suitable means such as a rounded gold tip 65. Spaced apart radiopaque markers of a suitable type such as gold bands 66 are carried by the guide wire 57 within the balloon near the proximal and distal extremities of the balloon 56 to define the working length of the balloon 56.

As described in conjunction with the balloons of the dilatation catheters shown in FIGS. 1-6, various approaches may be utilized for providing the self-venting feature to the catheter 51 and to its balloon 56. For example, as shown a plurality of micromachined holes 67 can be provided which extend longitudinally of the balloon 56 from the distal extremity of the same and over the crown or proximal crown of the balloon as shown in FIG. 7 and as explained previously. These holes 67 can be arranged in a myriad of patterns. They can have the same size as hereinbefore described. Alternatively, in place of a plurality of holes 67, a single hole (not shown) such as the hole 48 provided in FIG. 6 can be provided in the balloon and covered with a porous material. Alternatively, the balloon itself can be formed of a porous material such as disclosed with respect to the tubular member in FIG. 4.

It is apparent from the foregoing that various approaches can be utilized for venting the balloon so that when it is inflated with an inflation medium that air trapped in the balloon can escape to the atmosphere through a plurality of the small passages which are provided and which will not permit the passage of the balloon inflation medium therethrough.

What is claimed is:

1. A self-venting balloon dilation catheter comprising an elongate flexible tubular member with an inflatable balloon on the distal portion thereof, the tubular member having at least one lumen extending longitudinally therein to at least the interior of the balloon and in fluid communication therewith for inflating the balloon with a liquid inflation medium and the balloon having a wall portion adjacent an end thereof with a plurality of small micromachined holes therein having diameters from about 0.000015 to about 0.001 inch in fluid communication with the interior of the balloon permitting air to escape from the interior of the balloon but inhibiting the passage of the liquid inflation medium when the balloon is inflated thereby.

2. The dilatation catheter of claim 1 wherein the micromachined holes are disposed in the balloon wall longitudinally spaced from an end of the balloon.

3. The catheter of claim 1 wherein a port is provided in fluid communication with the interior of the balloon and a porous means covers said port.

4. A catheter as in claim 3 wherein said porous means covering said port is in the form of a porous plastic material.

5. A catheter as in claim 3 wherein said porous means covering said port is in the form of a porous metallic material.

6. A catheter as in claim 5 wherein said porous metallic material is a radiopaque material.

7. A self-venting balloon dilatation catheter comprising an elongated flexible tubular member having an inflatable dilatation balloon on the distal portion thereof, at least one lumen extending longitudinally therein to the interior of the inflatable balloon and adapted to direct liquid inflation fluid to the interior of the balloon for the inflation thereof, and a plurality of micromachined holes ranging in diameter from about 0.000015 to about 0.001 inch through the wall of the balloon adjacent an end thereof which permits the escape of air but not liquid from each interior of the balloon to the exterior of the balloon when the balloon is inflated with liquid inflation fluid.

8. A self-venting balloon dilatation catheter comprising an elongate flexible tubular member with an inflatable balloon on the distal portion thereof having at least one lumen extending longitudinally therein to the interior of the inflatable balloon and adapted to direct inflation liquid to the interior of the balloon and porous means forming a plurality of small circuitous passages permitting air but not liquid to escape from the interior of the balloon.

9. A catheter as in claim 8 wherein a port is provided in the tubular member in fluid communication with the interior of the balloon and porous means covers said port.

10. A self-venting balloon dilatation catheter comprising a first elongate flexible tubular member having an inner lumen extending longitudinally therethrough, a second elongate flexible tubular member coaxially disposed about said first tubular member and defining therebetween an annular lumen extending longitudinally of the same, a balloon carried by the second tubular member and in communication with the annular lumen and porous means having circuitous passageways therein which is secured to the first tubular member and is in fluid communication with the interior of the balloon for permitting air to escape from the interior of the balloon while inhibiting the escape of the liquid inflation medium from the interior of the balloon.

11. The dilation catheter of claim 10 wherein the first elongated flexible tubular member is provided with a port in fluid communication with the interior of the balloon and porous means covers the port.

12. The dilation catheter of claim 10 wherein the porous means is porous plastic.

* * * * *

UNITED STATES PATENT AND TRADEMARK OFFICE
CERTIFICATE OF CORRECTION

PATENT NO. : 4,821,722
DATED : April 18, 1989
INVENTOR(S) : Gary H. Miller et al.

It is certified that error appears in the above-identified patent and that said Letters Patent is hereby corrected as shown below:

Column 3, line 17, delete "form" and insert therefor --from--.

Column 3, line 23, delete "0.0005" and insert therefor --0.00015--.

Column 3, line 25, delete "for" (second occurrence) and insert therefor --from--.
Column 3, line 26, delete "36" and insert therefor --26--.

Column 3, line 26, delete "boon" and insert therefor --been--.

Column 3, line 27, delete "20" and insert therefor --26--.

Signed and Sealed this

Twelfth Day of November, 1991

Attest:

HARRY F. MANBECK, JR.

*Attesting Officer*   *Commissioner of Patents and Trademarks*

UNITED STATES PATENT AND TRADEMARK OFFICE
CERTIFICATE OF CORRECTION

PATENT NO.   : 4,821,722

DATED        : 4/18/89

INVENTOR(S)  : Gary H. Miller, et al

It is certified that error appears in the above-identified patent and that said Letters Patent is hereby corrected as shown below:

On the title page, Item [57]: Abstract, line 7, "inflating" should read --inflation--

Signed and Sealed this

Twenty-first Day of September, 1993

Attest:

BRUCE LEHMAN

Attesting Officer

Commissioner of Patents and Trademarks